(12) United States Patent
Dirkzwager et al.

(10) Patent No.: US 7,718,039 B2
(45) Date of Patent: May 18, 2010

(54) PROCESS FOR REACTIVE DISTILLATION OF A CARBOXYLIC ACID

(75) Inventors: Hendrik Dirkzwager, Amsterdam (NL); Leonardus Petrus, Amsterdam (NL); Catharina Johanna Maria Petrus-Hoogenbosch, legal representative, Amsterdam (NL); Pablo Poveda-Martinez, Amsterdam (NL)

(73) Assignee: Shell Oil Company, Houston, TX (US)

( * ) Notice: Subject to any disclaimer, the term of this patent is extended or adjusted under 35 U.S.C. 154(b) by 752 days.

(21) Appl. No.: 11/679,036

(22) Filed: Feb. 26, 2007

(65) Prior Publication Data

US 2007/0203358 A1 Aug. 30, 2007

(30) Foreign Application Priority Data

Feb. 28, 2006 (EP) .................................. 06110471

(51) Int. Cl.
*C07C 67/08* (2006.01)
*C07C 69/14* (2006.01)

(52) U.S. Cl. ........................................ 203/34; 560/265

(58) Field of Classification Search ........................ None
See application file for complete search history.

(56) References Cited

U.S. PATENT DOCUMENTS

| 6,028,215 A | 2/2000 | Bessling et al. | ............. 560/265 |
| 2002/0183545 A1 | 12/2002 | Lederer et al. | ............. 560/231 |

FOREIGN PATENT DOCUMENTS

| EP | 1300387 | 4/2003 |
| JP | 01193240 | 8/1989 |
| WO | 01/27065 | 4/2001 |

OTHER PUBLICATIONS

Dimian et al. Chemical Engineering and processing, 2004, vol. 43, pp. 411-420.*
Dimian et al: "Entrainer-enhanced reactive distillation" Chemical Engineering and Processing, vol. 43, 2004, pp. 411-420, XP009069727.

* cited by examiner

*Primary Examiner*—Daniel M Sullivan
*Assistant Examiner*—Yevegeny Valenrod
(74) *Attorney, Agent, or Firm*—Charles W. Stewart

(57) ABSTRACT

A process for reactive distillation wherein a carboxylic acid is reacted in a reaction section of a reactive distillation column with an alcohol under esterifying conditions in the presence of a catalyst to form an ester, wherein a first supply stream comprising the carboxylic acid, a second supply stream comprising the alcohol and a third supply stream comprising an inert entrainer are supplied to the reactive distillation column, wherein the first supply stream is supplied to the column at a first entry level located just above or at the top of the reaction section, the second supply stream is supplied to the column at a second entry level located in or just below the reaction section and below the first entry level, and the third supply stream is supplied to the column at a third entry level located in or below the reaction section and not above the second entry level and wherein a bottom stream comprising the ester formed and unreacted carboxylic acid is obtained and a top stream comprising unreacted alcohol, water and entrainer is obtained.

20 Claims, 1 Drawing Sheet

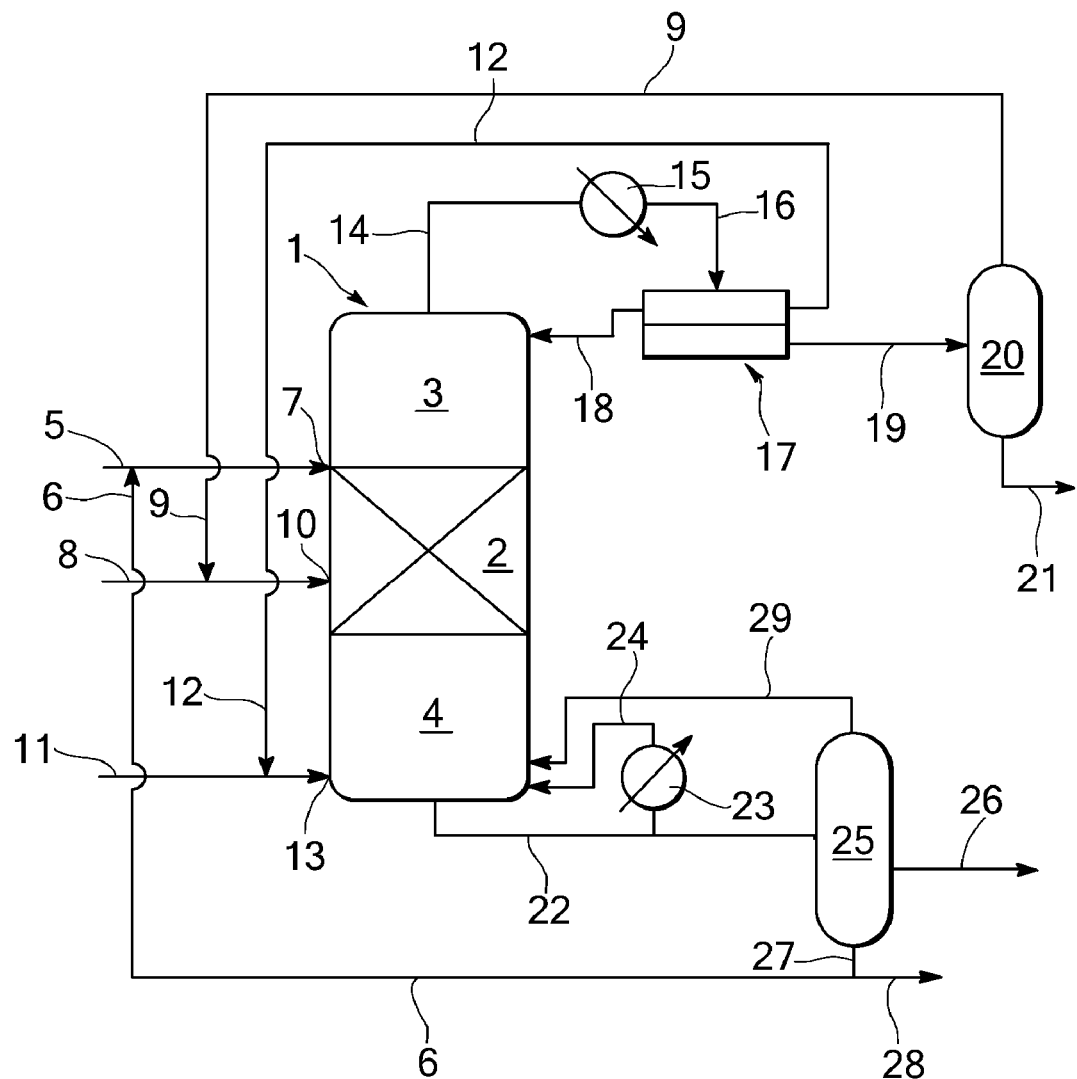

PROCESS FOR REACTIVE DISTILLATION OF A CARBOXYLIC ACID

CROSS-REFERENCE TO RELATED APPLICATION

This application claims priority from European Patent Application No. 06110471.7, filed on Feb. 28, 2006, which is incorporated herein by reference.

FIELD OF THE INVENTION

The present invention provides a process for reactive distillation wherein a carboxylic acid is reacted in a reaction section of a reactive distillation column with an alcohol under esterifying conditions in the presence of a catalyst to form an ester.

BACKGROUND OF THE INVENTION

Reactive distillation for esterification reactions is known. In WO 01/27065 for example, a reactive distillation process for the preparation of ethyl acetate is disclosed wherein ethanol is reacted with acetic acid and/or acetic anhydride in the presence of a solid acidic catalyst. Acetic acid or anhydride or their mixture and ethanol are introduced separately into the reactive distillation column.

In U.S. Pat. No. 6,028,215, a process for preparing esters from alcohol and carboxylic acid, in particular butyl acetate from butanol and acetic acid, is disclosed wherein an alcohol and a carboxylic acid are reacted in the presence of a heterogeneous acid catalyst.

A disadvantage of a reactive distillation process for the esterification of carboxylic acids with lower alcohols is that, in case the alcohol is not entirely consumed, a water/alcohol mixture is distilled over the top of the column. Recovery and recycling of the alcohol requires additional separation steps, usually one or more further distillation columns.

In a paper in Chemical Engineering and Processing 43 (2004) 411-420, Dimian et al. describe the use of a mass separation agent, usually called entrainer, in a reactive distillation process for the catalytic esterification of fatty acids with light alcohols that form homogeneous azeotropes with water. It is shown that adding an entrainer to the top of the distillation column overcomes limitations due to distillation boundaries. The entrainer enhances water removal from the reaction zone and, as a result, water can be separated from the top stream by simple decantation. In this paper the use of n-propyl-acetate as entrainer in the esterification of lauric acid with 1-propanol is exemplified. Hydrocarbons, both aliphatic and aromatic, oxygenates such as esters, ethers and ketones, and halogenated hydrocarbons are mentioned as suitable entrainers.

In EP 1 300 387, a process for the manufacture of an ester of lactic acid by reactive distillation over a heterogeneous catalyst is disclosed. An entrainer is used to separate water introduced with the reactants and water produced by the esterification reaction from the distillation column. The distillation column is filled with reactant alcohol and entrainer before start-up of the reaction. During the reactive distillation, additional entrainer may be added. It is not mentioned to which part of the column further entrainer is added.

SUMMARY OF THE INVENTION

It has now been found that a reactive distillation process for the conversion of a carboxylic acid and an alcohol into an ester can be improved by supplying an inert entrainer to the bottom part of the column, i.e. to the lower part of the reaction section or below the reaction section, preferably at an entry level below that of the alcohol.

Accordingly, the present invention provides a process for reactive distillation wherein a carboxylic acid is reacted in a reaction section of a reactive distillation column with an alcohol under esterifying conditions in the presence of a catalyst to form an ester, wherein a first supply stream comprising the carboxylic acid, a second supply stream comprising the alcohol and a third supply stream comprising an inert entrainer are supplied to the reactive distillation column, wherein the first supply stream is supplied to the column at a first entry level located just above or at the top of the reaction section, the second supply stream is supplied to the column at a second entry level located in or just below the reaction section and below the first entry level, and the third supply stream is supplied to the column at a third entry level located in or below the reaction section and not above the second entry level and wherein a bottom stream comprising the ester formed and unreacted carboxylic acid is obtained and a top stream comprising unreacted alcohol, water and entrainer is obtained.

The process according to the invention has several advantages compared to the prior art process wherein the entrainer is added to the top of the column. An advantage of the process according to the invention is that a higher conversion of carboxylic acid is obtained than in the prior art process. Another advantage is that the ester that can be separated from the bottom stream is less contaminated with water and alcohol than the ester that can be separated from the bottom stream in a process with entrainer added to the top of the column. A further advantage is that the total energy requirement is lower. Moreover, the process according to the invention can be operated with a lower alcohol-to-carboxylic acid ratio than the prior art process, resulting in a lower volume of recycle streams.

BRIEF DESCRIPTION OF THE DRAWING

The FIGURE schematically shows a diagram of the process according to the invention.

DETAILED DESCRIPTION OF THE INVENTION

In the process according to the invention, carboxylic acid, alcohol and an inert entrainer are supplied to a reactive distillation column. In the column, the carboxylic acid and the alcohol are reacted under esterification conditions in the presence of an esterification catalyst to form an ester and water.

The inert entrainer is a compound that is inert under the process conditions applied and that distils over the top of the column in the process according to the invention. The entrainer acts as a mass separation agent for the separation of water from alcohol. The entrainer preferably is a compound that can be easily separated from the other compounds that distil over the top of the column, i.e. alcohol and water. Preferably, the entrainer is a hydrocarbon, more preferably a hydrocarbon selected from benzene, toluene, hexane, or cyclohexane. Cyclohexane is a particularly preferred entrainer.

As esterification catalyst, any homogeneous or heterogeneous esterification catalyst known in the art may be used. Typically, esterification catalysts are strong acidic catalysts. Examples of suitable homogeneous strong acidic catalysts are strong mineral acids or sulphonic acids, such as sulphuric acid, p-toluene sulphonic acid, phosphoric acid, and nitric acid. Sulphuric acid is a particularly suitable homogeneous catalyst. Examples of suitable heterogeneous strong acidic catalysts are strong acidic ion-exchange resins like sulphonated polystyrene, acidic ZSM-5 zeolite and acidic beta zeolite. Preferably, the reactive distillation column contains a fixed arrangement of heterogeneous catalyst, since no additional catalyst/product separation step is needed with such arrangement.

The reactive distillation column to which the reactants and the entrainer are supplied contains a reaction section, i.e. a section wherein catalyst and the reactant carboxylic acid and reactant alcohol are present. The reactive distillation column comprises a rectifying section above the reaction section and a stripping section below the reaction section. Each of the sections comprise at least one separation tray or one theoretical separation stage.

In case a heterogeneous catalyst is used, the reaction section of the reactive distillation column contains solid catalyst in a fixed arrangement. The first supply stream comprising carboxylic acid will be supplied to the top tray or stage of the reaction section or just above, i.e. one or two trays or stages above the top tray or stage of the reaction section. The second supply stream comprising alcohol may be supplied to the column at an entry level in the reaction section at a level below the first entry level or just below the reaction section, i.e. in the range of from one to five, preferably one or two trays or stages below the lowest tray or stage of the reaction section. The third supply stream comprising entrainer may be supplied to the column at the same level as the second supply stream. Preferably, the third supply stream is supplied to the column at an entry level below the second entry level and below the reaction section.

In case an homogeneous catalyst is used, the catalyst is supplied to the reactive distillation column in the top tray or stage of the reaction section. The first supply stream may be supplied to the column at the same level as the catalyst, i.e. in the top tray/stage of the reaction section, or one or two trays/stages above the top of the reaction section. Preferably, the less volatile reactant, i.e. the first supply stream with the carboxylic acid, is supplied to the column at the same level as the homogeneous catalyst.

The homogeneous catalyst has a very low volatility and will therefore end up in the bottom stream of the reactive distillation column and thus be present at any level of the column below its entry level. Since the unreacted carboxylic acid and part of the unreacted alcohol will also end up in the bottom steam, the reaction section extends in case of an homogeneous catalyst to the bottom of the column. Therefore, the second and the third supply streams will, by definition, be supplied to the column in the reaction section. In case an homogeneous catalyst is used, the stripping section and the reaction section therefore overlap. The stripping section is in this case defined as the part of the column below the second entry level.

In order to minimise the amount of alcohol and water in the bottom stream, the third supply stream is preferably supplied to the column below the second supply stream, i.e. the third entry level is located below the second entry level. More preferably, the third supply stream is supplied to the column in the bottom tray or in the bottom theoretical separation stage, i.e. in the reboiler, or in the tray or stage directly above the bottom tray or stage.

The carboxylic acid and alcohol react with each other in the reaction section to form an ester and water. A bottom stream comprising the ester formed, unreacted carboxylic acid and heavy products formed and a top stream comprising unreacted alcohol, water and entrainer are withdrawn from the column. The bottom stream will typically comprise a few percentages of entrainer and may also comprises a few percentages of unreacted alcohol and a trace of water. It will be appreciated that the fractions of alcohol and entrainer that end up in the bottom stream strongly depend on the reboiler conditions such as pressure and temperature. In case an homogeneous catalyst is used, the bottom stream also comprises the catalyst. Typically, at least part of the bottom stream is vaporised in a reboiler and recycled to the bottom of the column for stripping the liquid stream from the reaction section.

The top stream is typically condensed in a condenser. Liquid entrainer may be separated from the condensed top stream by any liquid/liquid separation technique known in the art, for example by phase separation in a decanter. Preferably, part of the separated liquid entrainer is recycled to the top of the column for providing liquid reflux at the top of the column and the remainder of the separated liquid entrainer is recycled to the reactive distillation column as part of the third supply stream.

After separation of liquid entrainer from the condensed top stream, a liquid alcohol-water mixture is obtained that may be separated in a water-rich stream and an alcohol-rich stream in a distillation column for water separation. The alcohol-rich stream, which will typically comprise some water, is preferably recycled to the reactive distillation column as part of the second supply stream. In case the alcohol forms an homogeneous azeotrope with water, the composition of the alcohol-rich stream typically is the azeotropic composition.

The bottom stream is preferably fed to a product separation column for separation of an ester product stream from it. Preferably, the ester product stream is recovered as a side stream from the product separation column via a side draw-off, and a bottom stream comprising carboxylic acid and heavy products, and a top stream comprising entrainer and optionally alcohol are withdrawn from the product separation column. The top stream is preferably recycled to the reactive distillation column at a level that is not above the second entry level, more preferably below the second supply level. The top stream may be recycled to the reactive distillation column as part of the third supply stream or separately as a fourth supply stream. The bottom stream of the product separation column comprising unreacted carboxylic acid is preferably recycled to the reactive distillation column as part of the first supply stream, i.e. the supply stream comprising carboxylic acid. In order to prevent build-up of heavy products in the process, part of the bottom stream from the product separation column is preferably purged.

The carboxylic acid that is esterified in the process according to the invention may be any carboxylic acid that is liquid under distillative esterifying conditions. Suitable carboxylic acids may range from the light boiling formic acid to the high boiling fatty acids. Levulinic acid and pentanoic acid are particularly preferred carboxylic acids, since these acid biomass-derived acids may suitable be converted in a biomass-derived fuel component, i.e. a levulinate ester or a pentanoate ester, with the process according tot the invention.

The alcohol may be any alcohol that has a higher volatility than the reactant carboxylic acid and the product ester. Preferably, the alcohol is an alkyl alcohol comprising in the range of from 1 to 12 carbon atoms. More preferably, the alcohol is methanol, ethanol, 2-propanol, 1-butanol, or 1-pentanol. Ethanol is a particularly preferred alcohol.

Preferably, the carboxylic acid and the alcohol are chosen such that the ester formed has a higher volatility than the reactant carboxylic acid. If that is the case, the ester product stream can be separated from the bottom stream of the reactive distillation column by simple distillation in a product separation column and recovered from the process via a side draw-off from the product separation column. The heavy products and, in case of an homogeneous catalyst, the catalyst will then end up with the unreacted carboxylic acid in the bottoms of the product separation column and thus not contaminate the ester product stream. The process according to the invention is particularly suitable for the esterification of levulinic acid or pentanoic acid with ethanol.

If the process is a process for the esterification of levulinic acid or pentanoic acid with ethanol, the product ethyllevulinate or ethylpentanoate may suitably be used as fuel component, for example in gasoline or in diesel. In that case, cyclohexane is a particularly suitable entrainer, since an amount of up to a few percent of cyclohexane can be tolerated in diesel or gasoline. A particular advantage of the process according to the invention is that ethyllevulinate or ethyl-pentanoate can be recovered that has a very low content of ethanol. In diesel, the amount of ethanol should be minimised to avoid the negative effect of ethanol on the flash point of a diesel composition.

Suitably, the first supply stream comprising carboxylic acid is composed of a recycle stream comprising carboxylic acid separated from the bottom stream of the reactive distillation column and a make-up stream comprising carboxylic acid. The make-up steam may be a stream of substantially pure, i.e. at least 90 wt %, carboxylic acid. Alternatively, the make-up stream may be the effluent of a pre-converter for partially pre-converting carboxylic acid into its ester. If that is the case, the make-up stream comprises carboxylic acid, ester, some reaction water and optionally unconverted alcohol. In case an homogeneous esterification catalyst is used in the pre-converter, the effluent of the pre-converter may also comprise catalyst.

If the process according to the invention is operated without carboxylic acid recycle, the first supply stream only comprises make-up carboxylic acid, either in concentrated form or in the form of the effluent of a pre-converter.

The second supply stream comprises the reactant alcohol. Suitably, the second supply stream is composed of an alcohol make-up stream and a recycle stream. The recycle stream is a stream comprising alcohol and some water that is separated from the top stream of the reactive distillation column. The make-up stream may comprise some water. In case of an alcohol that forms an homogeneous azeotrope with water, the make-up stream suitable comprises alcohol and water in a ratio close to the azeotropic composition.

The third supply stream is suitably composed of a make-up stream of entrainer and a recycle entrainer stream. The recycle entrainer stream is entrainer that is separated from the top stream by cooling followed by phase separation. If there is an entrainer-comprising recycle stream that is separated from the bottom stream of the reactive distillation column, this recycle stream may also form part of the third supply stream. Alternatively, the entrainer-comprising recycle stream separated from the bottoms stream may be separately supplied to the reactive distillation column as a fourth supply stream.

Preferably, alcohol is supplied to the column in excess of the stoichiometric amount in order to shift the reaction equilibrium towards the ester product. More preferably, the amounts of alcohol and carboxylic acid supplied to the reactive distillation column, both in the make-up streams and the recycle streams, are such that the molar ratio of alcohol to carboxylic acid that is supplied to the column is in the range of from 2.0 to 12.0, even more preferably in the range of from 3.0 to 5.0.

In order to achieve phase separation between the entrainer phase and the alcohol/water phase of the condensed top stream, the molar ratio of entrainer to carboxylic acid supplied to the column is preferably in the range of from 5.0 to 20.0, more preferably of from 8.0 to 15.0.

The conditions in the reaction section of the reactive distillation column are esterification conditions, i.e. conditions at which the esterification reaction between carboxylic acid and alcohols occurs. The temperature in the reaction section preferably is in the range of from 50 to 250° C., more preferably of from 60 to 150° C. In case an heterogeneous catalyst that comprises macro-reticular ion-exchange resin is used, the temperature is preferably kept below the temperature at which catalyst degradation takes place. For sulphonated polystyrene, catalyst degradation usually takes place above 120° C., although some types of sulphonated polystyrene may suitably be operated at temperatures up to 150° C.

The process according to the invention is preferably operated such that the pressure in the top of the column is in the range of from 0.5 to 10.0 bar (absolute), more preferably in the range of from 0.8 to 5.0 bar (absolute). It will be appreciated that the operating temperature and pressure are chosen such that the top stream is still condensable and that the boiling temperature in the reboiler is such that the product ester is not degraded.

DETAILED DESCRIPTION OF THE DRAWING

In the FIGURE is shown a process scheme of the process according to the invention. A reactive distillation column 1 is shown that has a reaction section 2, a rectifying section 3 above reaction section 2 and a stripping section 4 below reaction section 2. Reaction section 2 contains a strong acidic macroreticular ion-exchange resin on a structured packing. Reaction section 2 has ten theoretical separation stages. Rectifying section 3 has ten theoretical separation stages and stripping section 4 has fifteen theoretical separation stages. A make-up stream of levulinic acid in line 5 and a recycle stream of levulinic acid in line 6 are supplied to column 1 at first entry level 7 located at the 10th theoretical separation stage, i.e. one stage above the top stage of reaction section 2. A wet ethanol stream composed of a stream of make-up ethanol from line 8 and a recycle stream of ethanol from line 9 is supplied to column 1 at second entry level 10 located at the 21st theoretical separation stage. A make-up stream of cyclohexane from line 11 and a recycle stream of cyclohexane from line 12 are supplied to column 1 at third entry level 13 located at the 34th theoretical separation stage. In reaction section 2, esterification takes place and ethyllevulinate and water are formed. A top stream comprising ethanol, water and cyclohexane is withdrawn from column 1 via line 14 and condensed in condenser 15. A condensed top stream is fed via line 16 to decanter 17 and separated in cyclohexane and a mixture of ethanol and water. Part of the cyclohexane is recycled to the top of column 1 via line 18 as rectifying liquid. The remainder of the cyclohexane is recycled to column 1 via line 12. The mixture of ethanol and water is fed via line 19 to water separation column 20 and separated in a water stream that is withdraw from column 20 via line 21 and a wet ethanol stream that is recycled to column 1 via line 9.

A bottom stream comprising levulinic acid, ethyllevulinate, heavy products and minor amounts of ethanol and cyclohexane is withdrawn from column 1 via line 22. Part of the bottom stream is vaporised in reboiler 23 and recycled via line 24 to the bottom of column 1 as stripping gas. The greater part of the bottom stream is fed to product separation column 25. A product stream of ethyllevulinate is obtained via side draw-off 26 of column 25. A bottom stream comprising levulinic acid and heavy products is withdrawn from column 25 via line 27. A small part of it is purged via line 28 and the greater part is recycled to column 1 via line 6. A top stream comprising ethanol and cyclohexane is withdrawn from product separation column 25 via line 29 and recycled to the 34th theoretical separation stage of column 1.

EXAMPLES

The process according to the invention is further illustrated by means of the following non-limiting examples. In each of the examples, a reactive distillation process for the esterification of levulinic acid to ethyllevulinate is simulated using RADFRAC software.

Example 1

No Entrainer; not According to the Invention

A reactive distillation is carried out in a distillation column with a diameter of 2.7 m, having 35 theoretical separation stages including a reaction section containing a bed (height of bed: 2.5 m) of heterogeneous esterification catalyst (Amberlyst 15 immobilised in a Sulzer Katapak-SP packing) having 10 theoretical separation stages ($11^{th}$ to $20^{th}$ stage) and 215 kg catalyst per stage, a rectifying section above the reaction section ($1^{st}$ to $10^{th}$ stage) and a stripping section below the reaction section having ($21^{st}$ to $35^{th}$ stage).

A first supply stream comprising levulinic acid of 13,214 kg/h (10,440 kg/h make-up stream comprising 98 wt % levulinic acid and 2 wt % water and 2,774 kg/h recycle stream) is supplied to the column at the stage above the reaction section, i.e. at the 10th stage. A second supply stream comprising 95.4 wt % ethanol and 4.6 wt % water of 15,127 kg/h (a make-up stream of 3848 kg/h and a recycle stream of 11,269 kg/h) is supplied to the column at the tray just below the reaction section (at the $21^{st}$ stage).

The reactive distillation column is operated with atmospheric pressure in the condenser and a pressure of 1.42 bar (absolute) in the reboiler. In the reaction section, esterification takes place. A top stream comprising water and ethanol is withdrawn from the column and condensed. Thirty percent of the condensed stream is refluxed to the top stage of the reactive distillation column and the remainder is fed to a water separation column to obtain a water-rich stream and a wet ethanol stream. The wet ethanol stream (11,269 kg/h) is recycled to the reactive distillation column with the make-up wet ethanol at the $21^{st}$ stage. A bottom stream comprising ethyllevulinate, unconverted levulinic acid, ethanol and heavy products is fed to a product separation column to obtain a product stream of ethyllevulinate as side stream, an ethanol stream as top stream and a bottom stream comprising the unreacted levulinic acid and heavy products. Part of the bottom stream is recycled to the reactive distillation column (2,774 kg/h) and supplied to it with the make-up levulinic acid at the 10th stage. The ethanol stream (28,081 kg/h) is recycled to the reactive distillation column at the $34^{th}$ stage. Each column comprises a reboiler and a condenser and part of the bottom stream and top stream is reboiled and condensed, respectively, and recycled to the bottom and top of the column, respectively.

The molar ratio of ethanol to levulinic acid supplied to the reactive distillation column (both in make-up streams and recycles) is 10.0.

Example 2

Entrainer Supplied to Top of Reaction Section; Not According to the Invention

In a reactive distillation column as described in EXAMPLE 1, wet ethanol is fed to the column one stage below the bottom stage of the reaction section, i.e. at the $21^{st}$ stage. Levulinic acid and entrainer (cyclohexane) are fed to the stage directly above the top stage of the reaction section, i.e. at the $10^{th}$ stage.

In the reaction section, esterification takes place. A top stream comprising cyclohexane, ethanol and water is obtained and a bottom stream comprising ethyllevulinate, unconverted levulinic acid, ethanol, and heavy products is obtained.

The top stream is condensed and fed to a decanter to obtain cyclohexane and a water/ethanol mixture. Thirty percent of the cyclohexane is refluxed to the top stage of the reactive distillation column and the remainder is recycled to the reactive distillation column at the $10^{th}$ stage. The water/ethanol mixture is separated in a water separation column to obtain a wet ethanol stream as top stream and water as bottom stream. The wet ethanol stream is recycled to the reactive distillation column at the $21^{st}$ stage.

The bottom stream of the reactive distillation column is fed to a product separation column and separated into ethyllevulinate as side stream, a top stream mainly comprising ethanol and a bottom stream comprising unconverted levulinic acid and heavy products. The top stream is recycled to the bottom of the reactive distillation column at the $34^{th}$ stage. Part of the bottom stream of the product separation column is recycled to the reactive distillation column and supplied to it with the fresh levulinic acid at the $10^{th}$ stage (the other part is purged).

The molar ratio of ethanol to levulinic acid supplied to the reactive distillation column (both in make-up steams and recycles) is 7.35. The molar ratio of cyclohexane to levulinic feed is 12.92.

Example 3

Entrainer to the Bottom of the Column; According to the Invention

In a reactive distillation column as described above in EXAMPLE 1 or 2 and as shown in the FIGURE, wet ethanol is fed to the reaction section at the $15^{th}$ stage. Levulinic acid is fed to the column at the stage directly above the top stage of the reaction section, i.e. at the $10^{th}$ stage. Entrainer (cyclohexane) is fed stage directly above the bottom stage of the column, i.e. at the $34^{th}$ stage.

In the reaction section, esterification takes place. A top stream comprising cyclohexane, ethanol and water is obtained and a bottom stream comprising ethyllevulinate, unconverted levulinic acid, ethanol, cyclohexane and heavy products.

The top stream is condensed and fed to a decanter to obtain cyclohexane and a water/ethanol mixture. Thirty percent of the cyclohexane is refluxed to the top stage of the reactive distillation column and the remainder is recycled to the reactive distillation column and supplied to it at the $34^{th}$ stage. The water/ethanol mixture is separated in a water separation column to obtain a wet ethanol stream as top stream and water as bottom stream. The wet ethanol stream is recycled to the reactive distillation column at the 15$^{th}$ stage.

The bottom stream of the reactive distillation column is fed to a product separation column and separated into ethyllevulinate as side stream, a top stream mainly comprising ethanol and cyclohexane and a bottom stream comprising unconverted levulinic acid and heavy products. The top stream is recycled to the bottom of the reactive distillation column at the 34$^{th}$ stage. Part of the bottom stream of the product separation column is recycled to the reactive distillation column and supplied to it with the make-up levulinic acid at the 10$^{th}$ stage (the other part is purged).

The molar ratio of ethanol to levulinic acid supplied to the reactive distillation column is 7.35. The molar ratio of cyclohexane to levulinic supplied to the reactive distillation column is 12.92.

Example 4

Entrainer to the Bottom of the Column; According to the Invention

As EXAMPLE 3, but with a molar ratio of ethanol to levulinic acid supplied to the column of 4.64.

In table 1 is shown for EXAMPLES 1 to 4 the flow rates of the different streams supplied to the reactive distillation column.

In table 2 is shown the performance of the reactive distillation column for EXAMPLES 1 to 4.

In table 3 is shown the performance of the product separation column for EXAMPLES 1 to 4 and in table 4 is shown the composition of the ethyllevulinate product stream that is withdrawn as side stream from the product separation column. In each of the examples, the product separation column has 22 theoretical separation stages and is operated at vacuum conditions, with a reboiler pressure of 0.036 bar (absolute). The feed, i.e. the bottom stream of the reactive distillation column is fed at the 17$^{th}$ stage (the top stage is the 1st stage).

In table 5 is shown the performance of the water separation column for EXAMPLES 1 to 4. In each of the examples, the water separation column has 45 theoretical separation stages. The water-ethanol feed mixture is fed to the 30$^{th}$ stage. The reboiler is operated at a pressure of 1.22 bar (absolute).

In table 6 is shown the composition of the wet recycle, i.e. the top stream from the water separation column, and the molar ratio between the water in the wet recycle and the ethyllevulinate formed.

TABLE 2

Performance of the reactive distillation column.

| example | per-pass conversion (wt % of levulinic acid feed) | reboiler duty (MW) | condenser duty (MW) | T reboiler (° C.) | T condenser (° C.) |
|---|---|---|---|---|---|
| 1 | 98.70 | 6.50 | 5.02 | 91.7 | 84.3 |
| 2 | 98.39 | 12.70 | 11.60 | 99.1 | 67.4 |
| 3 | 99.15 | 11.20 | 10.30 | 83.5 | 67.4 |
| 4 | 99.06 | 11.20 | 10.37 | 94.6 | 67.4 |

TABLE 3

Performance of the product separation column.

| example | reboiler duty (MW) | condenser duty (MW) | reflux ratio | T reboiler (° C.) | T condenser (° C.) |
|---|---|---|---|---|---|
| 1 | 10.00 | 4.49 | 0.55 | 181.8 | 0.5 |
| 2 | 6.20 | 4.48 | 1.70 | 178.4 | 0.1 |
| 3 | 10.00 | 7.32 | 1.70 | 148.2 | −2.9 |
| 4 | 2.15 | 1.76 | 2.50 | 177.8 | −16.4 |

TABLE 4

Composition of product

| | | composition of ethyllevulinate product stream (wt %) | | | |
|---|---|---|---|---|---|
| example | side-draw stage | levulinic acid | EtOH | H$_2$O | c-C6 * |
| 1 | 14 | 1.48 | 0.74 | 0.02 | — |
| 2 | 14 | 3.60 | 3.20 | 0.39 | <1.0 10$^{-9}$ |
| 3 | 14 | 0.06 | 0.33 | 4.0 10$^{-6}$ | 0.05 |
| 4 | 9 | 4.0 10$^{-5}$ | 0.002 | <1.0 10$^{-9}$ | 0.16 |

*c-C6: cyclohexane

TABLE 1

Mass flow rates in kg/h of the supply streams to the reactive distillation column.

| | levulinic acid supply (1$^{st}$ supply stream) | | | wet ethanol supply (2$^{nd}$ supply stream) | | | entrainer supply (3rd supply stream) | | recycle$^a$ | | | |
|---|---|---|---|---|---|---|---|---|---|---|---|---|
| example | total supply | make-up | recycle | total supply | make-up | recycle | total supply | make-up | from decanter | recycle (4th supply stream) | total supply | total recycle |
| 1 | 13,214 | 10,440 | 2,774 | 15,127 | 3,858 | 11,269 | — | | | 28,081$^b$ | 56,422 | 42,124 |
| 2 | 13,242 | 10,297 | 2,945 | 24,986 | 4,173 | 20,813 | 38,031 | 0 | 38,031 | 9,484$^b$ | 85,743 | 71,273 |
| 3 | 13,159 | 10,535 | 2,624 | 20,355 | 3,069 | 17,286 | 32,472 | 0 | 32,472 | 18,050$^c$ | 84,036 | 70,432 |
| 4 | 13,173 | 10,645 | 2,528 | 22,072 | 4,453 | 17,619 | 32,572 | 0 | 32,572 | 6,418$^d$ | 74,235 | 59,137 |

$^a$from top of product separation column
$^b$mainly (>98 wt %) ethanol
$^c$mainly (>98 wt %) ethanol/cyclohexane mixture
$^d$mainly (>98 wt %) cyclohexane

TABLE 5

Performance of the water separation column.

| example | reboiler duty (MW) | condenser duty (MW) | reflux ratio | T reboiler (° C.) | T condenser (° C.) |
|---|---|---|---|---|---|
| 1 | 10.00 | 10.20 | 2.5 | 105.3 | 77.9 |
| 2 | 19.44 | 19.48 | 3.0 | 94.8 | 65.7 |
| 3 | 14.67 | 14.62 | 2.5 | 99.6 | 67.2 |
| 4 | 14.93 | 14.88 | 2.5 | 99.9 | 67.1 |

TABLE 6

Water separation performance of the process.

| example | wet recycle composition (mole % EtOH/H$_2$O/c-C6*) | water in wet recycle (molar ratio H$_2$O/ethyllevulinate) |
|---|---|---|
| 1 | 85.4/14.5/- | 0.71 |
| 2 | 76.5/12.4/11.1 | 0.77 |
| 3 | 78.3/13.5/8.1 | 0.58 |
| 4 | 78.2/13.5/8.3 | 0.58 |

*c-C6: cyclohexane

The examples above show that in the process according to the invention (EXAMPLES 3 and 4), an ethyllevulinate product is obtained that has much lower amounts of water, ethanol and unconverted levulinic acid than in a process wherein the entrainer is supplied to the top of the column (EXAMPLE 2) or wherein no entrainer is used (EXAMPLE 1). See table 4 in this respect. In case a relatively low ratio of ethanol-to-levulinic acid is used (EXAMPLE 4), an even lower amount of water, ethanol and unconverted levulinic acid is found in the product stream. In that case, also the energy required for operating the product separation column is lowest (see Table 3).

The conversion of levulinic acid is higher in the process according to the invention (EXAMPLES 3 and 4) than in a process wherein the entrainer is supplied to the top of the column (EXAMPLE 2) or wherein no entrainer is used (EXAMPLE 1). See Table 2 in this respect.

Compared to a process wherein the entrainer is added to the top of the reaction section (EXAMPLE 2), the energy requirement for the process according to the invention (EXAMPLES 3 and 4) is lower. Further, it can be seen from Table 6 that the water separation is more efficient in the process according to the invention (EXAMPLES 3 and 4), since there is less water in the recycle streams.

What is claimed is:

1. A process for reactive distillation wherein a carboxylic acid is reacted in a reaction section of a reactive distillation column with an alcohol under esterifying conditions in the presence of a catalyst to form an ester, wherein a first supply stream comprising the carboxylic acid, a second supply stream comprising the alcohol and a third supply stream comprising an inert entrainer are supplied to the reactive distillation column, wherein the first supply stream is supplied to the column at a first entry level located just above or at the top of the reaction section, the second supply stream is supplied to the column at a second entry level located in or just below the reaction section and below the first entry level, and the third supply stream is supplied to the column at a third entry level located in or below the reaction section and not above the second entry level and wherein a bottom stream comprising the ester formed and unreacted carboxylic acid is obtained and a top stream comprising unreacted alcohol, water and entrainer is obtained.

2. A process according to claim 1, wherein the third entry level is located below the second entry level.

3. A process according to claim 1, wherein the third entry level is located in the bottom tray or the bottom theoretical separation stage of the reactive distillation column or in the tray or stage directly above the bottom tray or stage.

4. A process according to claim 1, wherein the carboxylic acid is levulinic acid or pentanoic acid.

5. A process according to claim 1, wherein the alcohol is an alkyl alcohol comprising in the range of from 1 to 12 carbon atoms.

6. A process according to claim 1, wherein the entrainer is a hydrocarbon.

7. A process according to claim 1, wherein the molar ratio of alcohol to carboxylic acid supplied to the column is in the range of from 2.0 to 12.0.

8. A process according to claim 1, wherein the molar ratio of entrainer to carboxylic acid supplied to the column is in the range of from 5.0 to 20.0.

9. A process according to claim 1, wherein the catalyst is a heterogeneous catalyst.

10. A process according to claim 1, further comprising separating a product stream comprising the ester formed from the bottom stream and recovering the product stream from the process.

11. A process according to claim 1, wherein the alcohol is methanol, ethanol, 2-propanol, 1-butanol or 1-pentanol.

12. A process according to claim 1, wherein the alcohol is ethanol.

13. A process according to claim 1, wherein the entrainer is a hydrocarbon selected from benzene, toluene, hexane or cyclohexane.

14. A process according to claim 1, wherein the entrainer is cyclohexane.

15. A process according to claim 1, wherein the molar ratio of alcohol to carboxylic acid supplied to the column is in the range of from 3.0 to 5.0.

16. A process according to claim 1, wherein the molar ratio of entrainer to carboxylic acid supplied to the column is in the range of from 8.0 to 15.0.

17. A process according to claim 2, wherein the third entry level is located in the bottom tray or the bottom theoretical separation stage of the reactive distillation column or in the tray or stage directly above the bottom tray or stage.

18. A process according to claim 2, wherein the carboxylic acid is levulinic acid or pentanoic acid.

19. A process according to claim 3, wherein the carboxylic acid is levulinic acid or pentanoic acid.

20. A process according to claim 2, wherein the alcohol is an alkyl alcohol comprising in the range of from 1 to 12 carbon atoms.

* * * * *